(12) United States Patent
Ke et al.

(10) Patent No.: US 9,243,241 B2
(45) Date of Patent: Jan. 26, 2016

(54) SEPARATION AND PURIFICATION OF NUCLEIC ACID FROM PARAFFIN-CONTAINING SAMPLES

(75) Inventors: Song-Hua Ke, San Diego, CA (US); Karl Hecker, San Diego, CA (US)

(73) Assignee: Life Technologies Corporation, Carlsbad, CA (US)

(*) Notice: Subject to any disclaimer, the term of this patent is extended or adjusted under 35 U.S.C. 154(b) by 1181 days.

(21) Appl. No.: 11/444,171

(22) Filed: May 31, 2006

(65) Prior Publication Data

US 2007/0026432 A1    Feb. 1, 2007

Related U.S. Application Data

(60) Provisional application No. 60/686,522, filed on May 31, 2005, provisional application No. 60/773,027, filed on Feb. 13, 2006.

(51) Int. Cl.
- *C12N 15/10* (2006.01)
- *C07H 1/00* (2006.01)
- *C12Q 1/68* (2006.01)

(52) U.S. Cl.
CPC .............. *C12N 15/1003* (2013.01); *C07H 1/00* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 5,672,696 A | * | 9/1997 | Wang et al. ................ 536/25.42 |
| 6,469,159 B1 | | 10/2002 | Belly et al. |
| 6,544,798 B1 | * | 4/2003 | Christensen et al. ......... 436/177 |
| 2005/0009045 A1 | | 1/2005 | Greenfield et al. |
| 2005/0059024 A1 | | 3/2005 | Conrad |

FOREIGN PATENT DOCUMENTS

| | | |
|---|---|---|
| EP | 0953635 | 11/1999 |
| JP | 11332562 | 11/1999 |
| JP | 2004514886 | 5/2004 |
| WO | WO-02/46463 | 6/2002 |
| WO | WO/02/48164 * | 6/2002 |
| WO | WO 2006/130632 | 6/2002 |
| WO | WO-2004/080579 | 12/2006 |

OTHER PUBLICATIONS

Sorg et al (1995 J. Clinical Microbiology 33: 821-823).*
06771657.1 Office Action Mailed May 18, 2010.
06771657.1 European Search Report mailed Feb. 4, 2010.
U.S. Appl. No. 11/552,063 Office Action Mailed Sep. 3, 2009.
U.S. Appl. No. 11/552,063 Office Action Mailed Apr. 27, 2010.
Stanta, et al., "RNA Extraction from Formalin-Fixed and Paraffin-Embedded Brain Tissues" Methods in Molecular Biology vol. 86, pp. 23-26, 1998.

* cited by examiner

*Primary Examiner* — Christopher M Gross
(74) *Attorney, Agent, or Firm* — Peter G. Foiles

(57) ABSTRACT

Disclosed are rapid and reproducible methods for separating and purifying nucleic acids from paraffin-containing tissue samples. The disclosed methods involve a melting step, where paraffin-containing tissue samples are heated in the presence of a detergent, causing the paraffin to melt and tissue sample cells to lyse. From the resulting two-phase mixture (i.e., a paraffin phase and an aqueous phase), the aqueous phase is collected for purification of nucleic acid. Protease(s) can be used at one or more points in the separation process to facilitate tissue cell lysis and/or degrade proteins that could degrade nucleic acid or interfere with subsequent genetic manipulation or analysis.

5 Claims, No Drawings

SEPARATION AND PURIFICATION OF NUCLEIC ACID FROM PARAFFIN-CONTAINING SAMPLES

CROSS REFERENCE TO RELATED APPLICATIONS

The present application claims the benefit of U.S. Provisional Patent Application No. 60/686,522, filed May 31, 2005 and U.S. Provisional Patent Application No. 60/773,027, filed Feb. 13, 2006. The entire content of both of these priority applications is incorporated heroin by reference.

TECHNICAL FIELD

The present disclosure relates to separation and purification of nucleic acids from paraffin-containing samples. More specifically, the disclosure relates to the separation and purification of nucleic acids from formalin-fixed paraffin-embedded (FFPE) tissue samples.

BACKGROUND

Genotyping and gene expression analyses of tissue samples can be of significant importance for the identification of disease biomarkers (e.g., genetic determinants), for the accurate diagnosis of disease, and for the determination of patients' course of treatment. Pharmacogenomic methods can identify patients likely to respond to a particular drug and lead to new therapeutic approaches. For example, tumor tissue excised from a patient can be analyzed for the increased or decreased expression of particular disease biomarkers and thereby help clinicians identify therapeutic agents that could be useful in treating the patient.

Genotyping and gene expression studies (e.g., by reverse transcriptase polymerase chain reaction (RT-PCR) amplification) of tissue samples often is performed using frozen tissue samples. However, many pathological samples are not prepared as frozen tissues, but rather are formalin-fixed and paraffin-embedded (FFPE) to allow histological analysis and archival storage. Thus, rapid and reliable methods for extracting nucleic acids from paraffin-containing tissue samples would greatly aid the study of disease mechanisms and biomarkers. The inventions disclosed herein address this need.

SUMMARY

Provided are methods for separating ribonucleic acid from a paraffin-containing sample, that involve: (a) heating the sample at about 50-85° C. for about 1-60 minutes in the presence of an ionic detergent to produce a paraffin phase and an aqueous phase; (b) removing the aqueous phase from the paraffin phase; and (c) adding a protease to the aqueous phase and incubating the aqueous phase at about 25-80° C. for about 5-60 minutes. In some embodiments, the paraffin-containing sample is a formalin fixed paraffin embedded (FFPE) tissue sample. In some embodiments, the heating is between about 64-85° C. In some embodiments, the heating is between about 60-75° C. In some embodiments, the heating is at about 72° C. In some embodiments, the heating is for about 1-30 min. In some embodiments, the heating is for about 10 min. In some embodiments, the ionic detergent is sodium dodecylsulfate (SDS), or Sarcosine. In some embodiments, the protease is Proteinase K. In some embodiments, the incubating is at about 35-70° C. In some embodiments, the incubating is at about 55-65° C. In some embodiments, the incubating is at about 56-58° C. In some embodiments, the incubating is for about 5-30 min. In some embodiments, the incubating is for about 10 min. In some embodiments, the methods further involve purifying the ribonucleic acid from the aqueous phase. In some embodiments, the purifying involves TRIZOL precipitation, guanidinium isothiocyanate, anion exchange chromatography, silica-based purification, ChargeSwitch® purification, or nucleic acid hybridization.

Also provided are methods for separating ribonucleic acid from a paraffin-containing sample, that involve: (a) heating the sample at about 50-85° C. for about 1-60 minutes in the presence of an ionic detergent to produce a paraffin phase and an aqueous phase; and (b) adding a protease to the aqueous phase and incubating the aqueous phase at about 25-80° C. for about 5-60 minutes. In some embodiments, the methods further involve removing the aqueous phase from the paraffin phase. In some embodiments, the paraffin-containing sample is a formalin fixed paraffin embedded (FFPE) tissue sample. In some embodiments, the heating is between about 64° C. and about 85° C. In some embodiments, the heating is at about 60-75° C. In some embodiments, the heating is at about 72° C. In some embodiments, the heating is for about 1-30 min. In some embodiments, the heating is for about 10 min. In some embodiments, the ionic detergent is SDS or Sarcosine. In some embodiments, the protease is Proteinase K. In some embodiments, the incubating is at about 35-70° C. In some embodiments, the incubating is at about 55-65° C. In some embodiments, the incubating is at about 56-58° C. In some embodiments, the incubating is for about 5-30 min. In some embodiments, the incubating is for about 10 min. In some embodiments, the methods further involve purifying the ribonucleic acid from the aqueous phase. In some embodiments, the purifying involves TRIZOL precipitation, guanidinium isothiocyanate, anion exchange chromatography, silica-based purification, ChargeSwitch® purification, or nucleic acid hybridization.

Also provided are methods for separating ribonucleic acid from a paraffin-containing sample, that involve heating the sample to about 50-85° C. for about 1-60 minutes in the presence of an ionic detergent and a protease to produce a paraffin phase and an aqueous phase. In some embodiments, the methods further involve removing the aqueous phase from the paraffin phase. In some embodiments, the paraffin-containing sample is a formalin fixed paraffin embedded (FFPE) tissue sample. In some embodiments, the heating is at about 64-85° C. In some embodiments, the heating is at about 60-75° C. In some embodiments, the heating is at about 65° C. In some embodiments, the heating is for about 1 min to about 30 min. In some embodiments, the heating is for about 10 min. In some embodiments, the ionic detergent is SDS or Sarcosine. In some embodiments, the protease is Proteinase K. In some embodiments, the methods further involve purifying the ribonucleic acid from the aqueous phase. In some embodiments, the purifying involves TRIZOL precipitation, guanidinium isothiocyanate, anion exchange chromatography, silica-based purification, ChargeSwitch® purification, or nucleic acid hybridization.

Also provided are methods for separating deoxyribonucleic acid from a paraffin-containing sample, that involve: (a) heating the sample at about 75-100° C. for about 1-60 minutes in the presence of a detergent to produce a paraffin phase and an aqueous phase; (b) removing the aqueous phase from the paraffin phase; and (c) adding a protease to the aqueous phase and incubating the aqueous phase at about 25-80° C. for about 5-60 minutes. In some embodiments, the paraffin-containing sample is a formalin-fixed paraffin embedded (FFPE) sample. In some embodiments, the heating is at about 85-100° C. In some embodiments, the heating is at about 100° C. In some embodiments, the heating is for about 1-30 min. In some embodiments, the heating is for about 10 min. In some embodiments, the detergent is an ionic detergent. In some embodiments, the ionic detergent is sodium dodecyl sulfate (SDS) or Sarcosine. In some embodiments, the detergent is a non-ionic detergent. In some embodiments, the non-ionic detergent is Triton X-114, NP-40 or Tween-20. In some embodiments, the protease is Proteinase K. In some embodiments, the incubating is at about 35-70° C. In some embodiments, the incubating is at about 55-65° C. In some embodiments, the incubating is at about 62° C. In some embodiments, the incubating is for about 5-30 min. In some embodiments, the incubating is for about 10 min. In some embodiments, the methods further involve purifying the deoxyribonucleic acid from the aqueous phase. In some embodiments, the purifying involves TRIZOL precipitation, guanidinium isothiocyanate, anion exchange chromatography, silica-based purification, ChargeSwitch® purification, or nucleic acid hybridization.

Also provided are methods for separating deoxyribonucleic acid from a paraffin-containing sample, that involve: (a) heating the sample to about 75-100° C. for about 1-60 minutes in the presence of a detergent to produce a paraffin phase and an aqueous phase; and (b) adding a protease to the aqueous phase and incubating the aqueous phase at about 75-100° C. for 5-60 minutes. In some embodiments, the paraffin-containing sample is a formalin-fixed paraffin embedded (FFPE) sample. In some embodiments, the heating is at about 85-100° C. In some embodiments, the heating is at about 100° C. In some embodiments, the heating is for about 1-30 min. In some embodiments, the heating is for about 10 min. In some embodiments, the detergent is an ionic detergent. In some embodiments, the ionic detergent is sodium dodecyl sulfate (SDS) or Sarcosine. In some embodiments, the detergent is a non-ionic detergent. In some embodiments, the non-ionic detergent is Triton X-114, NP-40 or Tween-20. In some embodiments, the protease is Proteinase K. In some embodiments, the incubating is at about 35-70° C. In some embodiments, the incubating is at about 55-65° C. In some embodiments, the incubating is at about 62° C. In some embodiments, the incubating is for about 5-30 min. In some embodiments, the incubating is for about 10 min. In some embodiments, the methods further involve the deoxyribonucleic acid from the aqueous phase. In some embodiments, the purifying involves TRIZOL precipitation, guanidinium isothiocyanate, anion exchange chromatography, silica-based purification, ChargeSwitch® purification, or nucleic acid hybridization.

Other features and advantages of the invention will be apparent from the following detailed description, and from the claims. The disclosed materials, methods, and examples are illustrative only and are not intended to be limiting. Skilled artisans will appreciate that methods and materials similar or equivalent to those described herein can be used to practice the invention.

Unless otherwise defined, all technical and scientific terms used herein have the meaning commonly understood by one skilled in the art to which this invention belongs. All publications, patent applications, patents, and other references mentioned herein are incorporated by reference in their entirety. In case of conflict, the present specification, including definitions, will control.

DETAILED DESCRIPTION OF THE INVENTION

Provided are materials and methods for the rapid separation and purification of nucleic acids from paraffin-containing samples. Methods of the invention may be used for separating and purifying nucleic acid from any paraffin-containing sample, including preserved (e.g., with formalin) tissue samples. Paraffin-containing samples may include tissue from any organism: vertebrate (e.g., mammals such as humans, primates, canines, felines, porcines, equines and bovines, as non-mammals such as birds, fish, amphibians and reptiles) or invertebrate (e.g., insects). Normal and diseased (e.g., tumor) tissue may be processed using the disclosed methods. Tumor types include those derived from skin, prostate, ovary, uterus, breast, lung, pancreas, small intestine, colon, liver, kidney, and brain.

Methods of the invention may be used for separating and purifying any nucleic acid, the quality of which is suitable for genetic manipulation (e.g., cloning, amplification, sequencing, RT-PCR and cDNA library construction), genotyping, and gene expression studies. Single stranded (ss) DNA, ssRNA (e.g., micro-RNA), double stranded (ds) DNA, and ds RNA may be separated and purified from paraffin-containing samples using the disclosed methods. The target nucleic acid may be linear or circular, and may be total RNA, mRNA, and chromosomal or genomic DNA (gDNA).

Methods of the invention generally involve a melting step, where paraffin-containing tissue samples are heated in the presence of a detergent, causing the paraffin to melt and tissue sample cells to lyse. From the resulting two-phase mixture (i.e., a paraffin phase and an aqueous phase), the aqueous phase is collected for purification of nucleic acid. Protease(s) can be used at one or more points in the separation process to facilitate tissue cell lysis and/or degrade proteins that could degrade nucleic acid or interfere with subsequent genetic manipulation or analysis. For example, a protease can be included before or during the melting step, and/or can be added to the aqueous phase of the two-phase mixture either before or after it is collected from the paraffin phase. These processes are further described herein.

Melting

In the melting step, a paraffin-containing sample is heated in the presence of a detergent, causing the paraffin to melt and tissue sample cells to lyse. For separation of RNA (e.g., mRNA), a paraffin-containing sample is heated at about 50° C. to 85° C. In some RNA-separation embodiments, the sample is heated at about 64° C. to 85° C., or at about 60° C. to 75° C. In one RNA-separation embodiment, the sample is heated at about 72° C. For separation of DNA (e.g., gDNA), a paraffin-containing sample is heated at about 75° C. to 100° C. In some DNA-separation embodiments, the sample is heated at about 85° C. to 100° C. In one DNA-separation embodiment, the sample is heated at about 100° C.

The melting step generally is performed for 1 to 60 minutes. In some embodiments, a paraffin-containing sample is heated for 1 to 30 minutes, or for 5 to 20 minutes. In one embodiment, the melting step is performed for about 10 min.

The melting step is performed in the presence of a detergent-containing buffer that facilitates cell lysis. The detergent-containing buffer may include one or more ionic and/or one or more non-ionic detergents. Suitable ionic detergents include sodium dodecyl sulfate (SDS), lauroylsarcosine, Na+ salt ("sarcosine" or Sarkosyl), bile salt detergents (e.g., CHAPS, CHAPSO, sodium deoxycholate, sodium taurocholate, sodium glychocholate, sodium glychodeoxycholate) and cetyltrimethylammonium bromide (CTAB). Nonionic detergents include sarcosine, Tween-20, NP-40, Triton X-100, NP-10, Triton X-114, Tween-80 and n-octanoyl-β-D-glucosylamine (NOGA). The detergent-containing buffer may also include a buffer salt such as Tris-HCl (pH 7.5-8.5), phosphates, HEPES, PIPES, MOPS, MES, TABS, TRICINE, NaCl, KCl, $MgCl_2$, a chelating agent (e.g., EDTA or EGTA), and/or a preservative.

Ionic and/or non-ionic detergents can be used for separation of RNA. In some embodiments, ionic detergents are used for separation of RNA. Ionic and/or non-ionic detergents can be used for separation of DNA. In some embodiments, non-ionic detergents are used for separation of DNA.

Aqueous Phase Collection

The melting step causes the paraffin to melt and tissue sample cells to lyse. From the resulting two-phase mixture (i.e., a paraffin phase and an aqueous phase), the aqueous phase is collected for purification of nucleic acid. Centrifugation can be used to facilitate separation of the paraffin and aqueous phases. For example, samples can be centrifuged at room temperature (or lower) at a suitable speed (e.g., maximal speed on a microcentrifuge) to facilitate separation of the paraffin phase from the nucleic acid-containing aqueous phase. The paraffin may solidify to form a layer above the aqueous phase. A pipette tip can be used to penetrate the paraffin layer to remove the aqueous phase.

Nucleic Acid Purification

Nucleic acids can be purified from the collected aqueous phase using any known method, including those that involve TRIZOL precipitation, ethanol precipitation, guanidinium isothiocyanate treatment, phenol-chloroform treatment, chromatography (e.g., anion exchange chromatography), silica-based purification, ChargeSwitch® purification (see PCT WO 99/29703 and PCT WO02/48164), nucleic acid hybridization, column chromatography, or magnetic bead based purification. Target RNA may be treated with DNase (e.g. DNase I) to degrade contaminating DNA. Target DNA may be treated with RNase (e.g. RNase I) to degrade contaminating RNA.

Use of Proteases

Protease(s) can be used at one or more points in the separation process to facilitate tissue cell lysis and/or degrade proteins that could degrade the target nucleic acid or interfere with its subsequent manipulation or analysis. For example, protease(s) can be included before or during the melting step (e.g., as a component of the detergent-containing buffer). Protease(s) also can be added to the aqueous phase of the two-phase mixture that results from the melting step, either before or after it is collected from the paraffin phase. Aqueous phase nucleic acids also can be applied to a substrate (e.g., affinity column) and subjected to protease treatment while associated with the substrate.

Any protease can be used for the separation methods described herein. In some embodiments, a proteases of a thermophilic bacterium such as *Thermus Aquaticus, Thermus filiformis, Thermotoga neapolitana, Thermotoga maritime* and *Thermococcus zilligi*, (e.g., *Thermus* sp. strain RT41a thermostable alkaline protease (Peek et al., *Eur. J Biochem.* 207:1035-1044, 1992) and EA1 protease (Moss et al., *Int. J. Legal Med.* 117:340-349, 2003)) is used. In one embodiment, Proteinase K is used.

In embodiments where a protease is added to the aqueous phase that results from the melting step, the protease can be incubated in the aqueous phase (either before or after it is collected from the paraffin phase) at about 25° C. to 80° C. (e.g., about 35° C. to 70° C., about 50° C. to 70° C., about 55° C. to 65° C., about 55° C. to 60° C., about 60° to 65° C., about 56° C. to 58° C., or about 62° C.). Such protease digestion generally is performed for about 5-30 minutes (e.g., about 10-20 minutes, or about 10 minutes). In one embodiment, Proteinase K digestion is performed for about 10 min at a temperature between 56° C. and 58° C.

Protease treatment, whether during the melting step or after separation of the resultant aqueous phase, may be performed in the presence of a chelating agent (e.g., EDTA or EGTA) present at about 1 to 500 mM (e.g., about 1 to 100 mM). Chelation of divalent cations such as magnesium can inhibit or prevent RNA degradation, as most RNases are magnesium-dependent. Advantageously, EDTA does not appear to significantly inhibit Proteinase K activity in the methods of the invention.

Further Processing—DNA Repair

DNA (e.g., gDNA) obtained by the methods disclosed herein can be treated with a translesion DNA polymerase to repair DNA damage (e.g., sustained during storage and removal from paraffin). A non-translesion DNA polymerase (e.g., containing 3'-5' exonuclease activity like the Klenow fragment of *E. coli* DNA polymerase 1) can be included during translesion DNA polymerase treatment.

Translesion DNA polymerases function in the replication of damaged DNA. Translesion DNA polymerases belong to the "UmuC/DinB/Rad30/Rev1" superfamily of DNA polymerases; named for the four prototypic genes that define the subfamilies of the translesion DNA polymerase superfamily. Translesion DNA polymerases include *E. coli* pol IV and pol V, and eukaryotic pol zeta, eta, iota, kappa, and theta. Some translesion DNA polymerases are mesophilic (e.g., Pol IV and Pol V from *E. coli*; Pol kappa from *S. cerevisiae, S. pombe*, human, mouse, *Drosophila*; Pol zeta from *S. cerevisiae*, human, mouse; Pol eta from *S. cerevisiae*, human, mouse; Pol iota from mouse, human) and others are thermophilic/thermostable (e.g., Pol IV from *B. stearothermophilus, S. sofataricus*).

EXAMPLES

Example 1

Heat vs. Chemical Processing of FFPE Tissue Samples

Three to eight pieces of 5 to 10 micron sections of FFPE mouse brain, kidney or heart tissue samples were placed into 1.5 ml Eppendorf tubes. 300 µl of Proteinase K digestion buffer (100 mM NaCl, 10 mM Tris-HCl, pH 8.0; 25 mM EDTA, pH 8.0 and 0.2-0.8% SDS) were added, and the tubes were spun in a microcentrifuge for 10 to 20 sec at maximum speed. The sample was incubated for 10 minutes at 72° C. with intermittent gentle mixing (2 to 3 times every 2-3 minutes). The sample was then centrifuged at maximum speed (13000-16000×g) for 1 minute to facilitate separation of the paraffin phase from the nucleic acid-containing aqueous phase. A clean pipette tip was used to penetrate the paraffin layer and collect the aqueous phase.

For comparison, FFPE mouse brain and heart tissue samples were processed using the organic solvent citrosol. Deparaffinization was performed by adding 1 ml citrosol to the FFPE tissue sections for 30 min with two changes, followed by 100% and 75% ethanol for 30 min with two changes. After a washing step with PBS for 15 min in two changes, 500 µl of lysis buffer (100 mM NaCl, 10 mM Tris-HCl, pH 8.0; 25 mM EDTA, pH 8.0 and 0.2-0.8% SDS) was added and samples were incubated at 52° C. overnight until all tissue fragments were completely dissolved (Shi et al. *J. Histochem Cytochem* 50:1005-1011, 2002).

10 µl of Proteinase K (20 mg/ml) or 20 µl of Protein Degrader (Invitrogen Corporation, Carlsbad, Calif., cat #R57001) were added to the nucleic acid-containing solutions produced as described above, the samples were mixed well and incubated at 58° C. for 10-15 min with occasional mixing. The sample was then briefly centrifuged at maximum speed in a microfuge.

Nucleic acid binding buffer (50 mM Tris-HCl, pH 7.5, 25 mM EDTA, pH 8.0, 4 M guanidine isothiocyanate) (400 µl) and 100% ethanol (800 µl) were added to the sample, followed by brief vortexing (total volume=1200-1500 µl). 700 µl of the solution was loaded onto a GF (F or G) RNA Cartridge column (RNA Cartridge) and centrifuged at maximum speed for 1 minute. The filtrate was discarded. About 700 µl of the remaining solution was transferred to the same column and the previous step was repeated. The column was washed with 500 µl of wash buffer II (Invitrogen cat #12183018) and the filtrate was discarded. The RNA cartridge column was placed into a new collection tube. The column was washed with 500 µl of wash buffer II and the filtrate was discarded. The washing step was repeated one more time. The column was then centrifuged for 1 minute to remove any liquid from the cartridge. The RNA cartridge column was placed into a new 2 ml collection tube and 40 µl RNase-free water or Tris-EDTA (TE) buffer were added. The column was incubated at room temperature for 1 minute, and centrifuged at maximum speed (12,000-14,000 rpm) to elute the RNA. A second elution with 40 µl water or TE buffer also can be performed.

In some experiments, total RNA was digested with DNase I (Invitrogen cat #18068-015) to degrade contaminating genomic DNA as described in the manufacturer's instructions. Total RNA was aliquoted and used for PCR or reverse transcription immediately or after storage at −80° C. RT-PCR was carried out using SuperScript™ III (Invitrogen cat#180800511) or ThermoX RT (cat#11150-025). PCR was carried out using Platinum Taq DNA Polymerase (Invitrogen cat#10966018).

The total yield of RNA for heat-processed samples was either equal to or greater than the chemically processed samples. Extracted total RNA was either untreated or treated with DNase I for comparison. Less gDNA was observed for heat-processed samples than for chemically processed samples.

RT-PCR reactions using DNase I-digested RNA samples prepared from mouse brain tissue as described above were performed in a volume of 25 µl for 35 cycles using the following parameters: 30 sec; 56° C. for 30 sec and 72° C. for 40 sec. The target gene amplified was mouse β-actin. Aliquots of 8 µl of PCR products were analyzed by electrophoresis a 2% agarose E-gel (Invitrogen). RT-PCR using heat-processed samples resulted in linger amplification products than RT-PCR using chemically processed samples.

Example 2

Effect of Detergents on RNA Separation

SDS-containing lysis buffer was compared to lysis buffers in which the SDS was either supplementing or replaced with other detergents. Total RNA was isolated from 6 pieces of mouse kidney FFPE tissue as described above. Duplicate samples were tested. Table 1 shows the detergents that were used in the six different lysis buffers.

TABLE 1

| Buffer number | Detergent(s) |
| --- | --- |
| 1 | 0.5% SDS |
| 2 | 0.5% SDS + 1% sarcosine |
| 3 | 0.5% Triton X-114 |
| 4 | 0.5% NP-40 |
| 5 | 0.5% Tween-20 |
| 6 | 1% sarcosine |

The Quant-iT RNA Assay Kit (Molecular Probes, Eugene, Oreg., cat# Q33140) was used to estimate the total RNA yield. Samples were optionally treated with DNaseI by adding 2 µl DNase I solution (1 unit/µl, amplification grade) to 25 µl of purified RNA and 3 µl 10× reaction buffer, then incubating at room temperature for 10 minutes. 2% E-gels (Invitrogen cat# G6018-02 were used to examine the total RNA.

The effect of the detergents used in the lysis buffer on the yield of RNA was examined. Less RNA was observed when lysis buffers containing the non-ionic detergents Triton X-114, NP-40 or Tween-20 were used. When using lysis buffers containing the ionic detergents SDS, Sarcosine or a combination of both, more RNA was observed. Comparison of DNase I-treated and DNase I-untreated samples confirmed that the isolated nucleic acid was RNA and that little contaminating DNA was present.

DNase I-treated RNA was used as template for RT-PCR as described above. PCR cycling conditions were as follows: denaturing at 94° C. for 30 sec, annealing at 56° C. for 30 seconds, extension at 72° C. for 40 sec. A 311 bp fragment of the β-actin gene was amplified. 5-7 µl of each RT-PCR reaction were analyzed by gel electrophoresis.

Example 3

Effect of Detergents on Genomic DNA Separation

Genomic DNA was isolated from 5 pieces of mouse liver FFPE tissue. A modified heating protocol for the separation of gDNA from FFPE tissue was followed. Briefly, 300 µl of melting buffer was added to each tube containing FFPE tissue sections. Two samples were processed for each group. The detergents used in the lysis buffer were the same as those shown in Table 1, plus another buffer (buffer 7) was used which contained 1% cetyltrimethylammonium bromide (CTAB). Samples were incubated at 100° C. for 10 minutes, then centrifuged for 1 min at 12,000 rpm. The aqueous phase under the wax layer was transferred to a new tube, then digested with Proteinase K (20 mg/ml) at 62° C. for 10 min with occasional mixing. Guanidine HCl (300 µl of 7.5 M) was added to each tube and the samples were heated at 100° C. for 10 min. Samples were mixed with 200 µl of 100% ethanol, then applied to a GF RNA cartridge column and washed as described above. Samples were eluted with 40 µl ddH$_2$O. Absorbance values at 260 nm were used to estimate total amounts of nucleic acids isolated. RNase A treatment was performed according to the manufacturer's protocol (Invitrogen). gDNA was examined on a 2% agarose gel and nucleic acid samples before and after RNase A digestion.

Table 2 shows the nucleic acid concentration of gDNA extracts obtained using buffers 1-7, as determined by the absorbance value at 260 nm (OD260). The OD260/OD280 ratios confirm that very little protein was present in the samples.

TABLE 2

| Sample    | Concentration | OD260/OD280 |
|-----------|---------------|-------------|
| Buffer #1 | 103.269       | 1.973       |
| Buffer #2 | 63.769        | 1.838       |
| Buffer #3 | 74.259        | 1.951       |
| Buffer #4 | 56.799        | 1.852       |
| Buffer #5 | 59.404        | 1.953       |
| Buffer #6 | 62.323        | 1.830       |
| Buffer #7 | 4.883         | 1.291       |

Aliquots (1.2 µl) of extracted gDNA were subjected to 30 cycles of PCR amplification in a total reaction volume of 25 µl using the following cycling conditions: denaturing at 94° C. for 30 sec, annealing at 56° C. for 30 seconds, extension at 72° C. for 40 sec with Platinum Taq DNA polymerase (Invitrogen, cat #11306-016). A 413 bp fragment of the mouse phosphorylae kinase (PGK-1) gene was amplified. An aliquot (7 µl) of each PCR reaction was analyzed by electrophoresis on a 2% agarose gel.

Example 4

Proteinase K Digestion on a Silica Membrane

Seven pieces of 10 µM sections of FFPE mouse liver tissue samples were placed into a 1.5 ml Eppendorf tube. 300 µl of Proteinase K digestion buffer (100 mM NaCl, 10 mM Tris-HCl, pH 8.0; 25 mM EDTA, and 0.5% NP-40) were added, and the tube was spun in a microcentrifuge for 10 seconds at maximum speed. The sample was incubated for 10 minutes at 95° C. with intermittent gentle mixing (2 to 3 times every 2-3 minutes). The sample was then centrifuged immediately at maximum speed (13000-16000×g) for 1 minute to facilitate separation of the paraffin phase from the nucleic acid-containing aqueous phase. A clean pipette tip was used to penetrate the paraffin layer and collect the aqueous phase to transfer it to a new 1.5 ml tube.

20 µl of Proteinase K (20 mg/ml) was added to the nucleic acid-containing solutions produced as described above, and the sample was mixed well and incubated at 62° C. for 60 minutes with occasional mixing. Nucleic acid binding buffer (500 µl) containing 7.5 M guanidine hydrochloride was added and the sample was incubated at 72° C. for 30 minutes. 100% ethanol (500 µl) was added to the sample, followed by brief vortexing. 700 µl of the sample was loaded onto a silica spin column and centrifuged at maximum speed for 1 minute. The filtrate was discarded. About 700 µl of the remaining solution was added to the same column and the previous step was repeated to allow the entire sample to go through the column. The column was washed with 500 µl of washing buffer and the filtrate was discarded. The washing step was repeated once. 100 µl of Proteinase K solution (2 mg/ml) was added to the column followed by incubation at 62° C. for 30 minutes. (For a control group this $2^{nd}$ Proteinase K on-column digestion was omitted.) The column was washed with 500 µl washing buffer and washing was repeated two more times. gDNA was eluted from the column with 40 µl heated water (72° C.) and elution was repeated with 40 µl heated water. The OD of the nucleic acid sample was confirmed and run on a gel to examine the quality and yield of gDNA.

Nucleic acid samples isolated with or without $2^{nd}$ Proteinase K on-column digestion were compared by digesting genomic DNA with Nsp I restriction enzyme and ligating with Nsp I adaptor (Affymetrix part no. #900766.1). After ligation, PCR was used to amplify the DNA and 5 µl of PCR product was applied to a 1% agarose gel and subjected to electrophoresis to examine the PCR products. gDNA isolated using the $2^{nd}$ Proteinase K on-column digestion generated longer PCR products than gDNA isolated without the $2^{nd}$ digestion.

Example 5

Isolation of Micro-RNA from FFPE Tissues

Eight pieces of 10 µm sections of FFPE mouse liver samples were placed into a 1.5 ml tube. 300 µl of Proteinase K digestion buffer was added to the tube and vortexed for 10 seconds at top speed. The sample was incubated at 10 minutes at 72° C. with intermittent gentle mixing (2 to 3 times every 2-3 minutes). The sample was then immediately centrifuged at top speed (13000-16000×g) for 1 minute to facilitate separation of the paraffin phase from the nucleic acid-containing aqueous phase. A clean pipette tip was used to penetrate the paraffin layer and collect the aqueous phase to transfer it to a new 1.5 ml tube.

10 µl of Proteinase K (20 mg/ml) was added to the nucleic acid-containing solution produced as described above, the sample was mixed well and incubated at 62° C. for 10 minutes with occasional mixing. 300 µl of Nucleic Acid Binding buffer and 323 µl 100% ethanol were added to the tube. The nucleic acid-containing mixture was then transferred to a silica spin column and centrifuged at top speed for one minute. Filtrate was collected and equally divided into two separate tubes. 740 µl of 100% ethanol was added to each tube. The tubes were vortexed and each of the samples was loaded into a mini column (Invitrogen cat. #K1550-05) and centrifuged at maximum speed for 1 minute. The filtrates were discarded and the mini columns were washed with 500 µl washing buffer from the Purelink FFPE kit (Invitrogen cat. #K1560-02) and repeated two more times. 10 µl RNase free water was used to elute the RNA from the mini columns. A second elution was performed using another 10 µl of RNase free water.

The concentrations of the isolated RNA samples were checked using a Nanodrop™ Spectrophotometer. RNA isolated using the mini column had concentrations between 182-248 ng/µl and the OD260/OD280 ratios (which were 1.89 to 1.91) confirmed that very little protein was present.

The isolated mouse liver RNA samples were also examined using a 15% TBE/Urea Polyacrylamide Gel. 4 µl of RNA samples were applied to each well and electrophoresis was performed at constant voltage of 180 volts for 55 minutes. Results indicated that micro RNA isolated using the mini column procedure ranged between 15 to 75 bases long.

Example 6

DNA Repair Using Primer Extension Assay with Translesion DNA Polymerase

Genomic DNA was purified as in Example 4, above. Primer extension reactions were prepared by combining 5 µl 10× Buffer II, 1.25 µl 10 µM dNTP, 2.5 µl 0.25 µM N6 random primer (Invitrogen Cat. #48190-011), 2.5 µg gDNA, and water added to a final volume of 48.75 µl. Reaction mixtures were heated to 94° C. for two minutes and immediately transferred to ice for one minute. While incubating on ice, 1.25 µl of enzyme mixture containing Klenow exo-DNA polymerase and Rad 30 DNA polymerase at a 100:1 ratio was added to the reaction tube. Reaction mixtures were incubated on ice for 5 minutes, room temperature for 10 minutes, 37° C. for one hour, 58° C. for 20 minutes and then maintained at 4° C.

Invitrogen's BioPrime Array CGH genomic labeling system (Invitrogen Cat. #18095-011) was used to label the gDNA isolated from FFPE tissues (with or without primer extension using translesion DNA polymerase) according to the manufacturer's kit-recommended protocol. Briefly, 500 ng of gDNA and 30 µl/ml random primers were incubated at 37° C. for two hours with Cy3-dCTP and Cy5-dCTP and DNA was subsequently purified with Purelink Purification Kit (Invitrogen Cat. #18095-013). DNA samples were analyzed using a Nanodrop™ Spectrophotometer and subjected to electrophoresis on a 6% TBE urea gel.

Dye incorporation after labeling was calculated and the results indicated that primer extension increased the dye incorporation efficiency for both Cy3 and Cy5 labeling of gDNA. Translesion DNA polymerase treatment improved the quality of the gDNA isolated from FFPE and aids in efficiency of downstream applications, in this case, higher Cy3 and Cy5 labeling efficiency.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for separating micro ribonucleic acid from a paraffin-containing sample comprising:
    (a) heating the sample at a temperature of from 50° C. to 85° C. for from 1 to 60 minutes in the presence of an ionic detergent and a protease,
    (b) remove the aqueous phase from the sample,
    (c) add ethanol to the aqueous phase to a final concentration of 35% and apply to a first silica column,
    (d) collect the eluate from the silica column of step (c),
    (e) adjust the ethanol concentration of the eluate of step (d) to 75% and apply to a second silica column and;
    (f) elute the micro ribonucleic acid from the second silica column using water.

2. The method of claim 1, wherein the ionic detergent is sodium dodecyl sulfate.

3. The method of claim 1, wherein the protease is Proteinase K.

4. The method of claim 1, wherein the sample is heated for 10 minutes at 75° C.

5. The method of claim 1, wherein the micro ribonucleic acid is from 15 to 75 bases long.

* * * * *